United States Patent
Milkowski et al.

(10) Patent No.: US 7,323,624 B2
(45) Date of Patent: Jan. 29, 2008

(54) METHOD FOR INFLUENCING THE CONTENT OF SINAPINE IN TRANSGENIC PLANT CELLS AND IN PLANTS

(75) Inventors: Carsten Milkowski, Halle (DE); Alfred Baumert, Halle (DE); Dieter Strack, Wolfenbüttel (DE)

(73) Assignee: Institut fur Pflanzenbiochemie, Halle/Saale (DE)

( * ) Notice: Subject to any disclaimer, the term of this patent is extended or adjusted under 35 U.S.C. 154(b) by 683 days.

(21) Appl. No.: 10/340,811

(22) Filed: Jan. 13, 2003

(65) Prior Publication Data
US 2003/0145354 A1    Jul. 31, 2003

(30) Foreign Application Priority Data
Jul. 14, 2000 (DE) ................................ 100 34 320
Jul. 16, 2001 (WO) ..................... PCT/EP01/08199

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. ..................... 800/306; 800/281; 800/285; 800/286; 800/287; 800/298; 435/320.1

(58) Field of Classification Search ............... 536/23.1, 536/23.2, 23.6; 800/278, 281, 285, 286, 800/298, 306
See application file for complete search history.

(56) References Cited

OTHER PUBLICATIONS

Milkowski C. et al. Planta 2000; vol. 211, pp. 883-886.*
Lim E. et al. The Journal of Biological Chemistry, Feb. 9, 2001; vol. 276, No. 6, pp. 4344-4349.*
GenBank Accession AB019232.*
Database EMBL Online!; Jan. 1, 1998; Database acession No. 023401 XP002201199.
M. Milkowski; "Cloning and Heterologous Expression of a Rape cDNA Encoding UDP-glucose; sinapate glucosyltransferase"; Planta, vol. 211, 2000, pp. 883-886, XP002201197.
Database EMBL Online!; Aug. 11, 2000; Database acession No. AF287143 XP002201200.
Lim Eng-Kiat, et al.; "Identification of glucosyltransferase genes involved in sinapate metabolism and lignin synthesis in Arabidopsis"; Journal of Biological Chemistry, American Society of Biological Chemists, Baltimore, MD, US, vol. 276, No. 6, Feb. 9, 2001, pp. 4344-4349, XP0021272233; ISNN: 0021-9258.
Schawn, X., et al.; "enzymology of UDP-glucose: sinapic acid glucosyltransferasefrom *Brassica napus*" Phytochemistry, vol. 49, No. 2, 1998, pp. 307-318, XP004290102.

* cited by examiner

*Primary Examiner*—Russell P. Kallis
(74) *Attorney, Agent, or Firm*—Kenyon & Kenyon LLP (57) ABSTRACT

The invention relates to a method for influencing the sinapine content in transgenic plant cells and plants. In particular, the invention relates to the inhibition of the enzymatic activity of a UDP-glucose: sinapate glucosyltransferase (SGT) in transgenic plant cells. The invention further relates to nucleic acid molecules containing a DNA sequence which codes for a protein with the enzymatic activity of an SGT. The invention furthermore relates to transgenic plants and plant cells comprising a nucleic acid molecule according to the invention, as a result of which contain a lower content of sinapine in comparison with wild-type plants or cells, and the agricultural products and propagating material of the transgenic plants.

32 Claims, 1 Drawing Sheet

Plasmid construction for dsRNAi-suppression of SGT gene expression

Figure 1

PCR-Amplification of a 5'-truncated FAD2-Intron from Arabidopsis

Cloning of the 5'-truncated FAD2-Intron as SmaI-BamHI-Fragment in pBNN pBNN-FS PCR-amplification of the appropriate cDNA-Fragments From B.napus SGT1 (about 470 bp 5') and Arabidopsis SGT (about 250 bp 5')

Cloning in antisense (NcoI-SmaI-Fragment) and sense (NheI-BamHI-Fragment) Directions in pBNN-FAD2is vector pBNN-sup-nap Cloning of the SGT-dsRNAi-fragment as NotI (blunted)-HindIII-fragment in binary vector pLH7000

SEQUENCE LISTING

<160> NUMBER OF SEQ ID NOS: 3

<210> SEQ ID NO 1
<211> LENGTH: 1715
<212> TYPE: DNA
<213> ORGANISM: Brassica napus

<400> SEQUENCE: 1

```
gaaaaacaga gcacacagaa gagaacccct ttttgaagga tggaactatc atcttctcct      60
ttacctcctc atgttatgct tgtatccttc ccaggacaag gccacgttaa tccacttctt     120
cgtctcggca agctcttagc ttcgaagggt ttactcgtca cttttgtcac cacagaatca     180
tggggcaaaa agatgcgaac cgccaacaag attcaagacc gagccctcaa acctatcggt     240
aaaggttatc tccggttcga tttcttcaac gatgggctcc ctgaagacga cgatgcaagc     300
agaaccaact taaccatcct ccgaccacaa ctcgagctgg tcggacaaca agagatcaaa     360
aacctcgtga aacgttacaa ggaagtgatg aaacagcccg tgacgtgtct catcaacaac     420
cctttcgtct cttgggtctg tgacgtagcc gaagatcttc aaatcccctg tgctgttctc     480
tgggtccagt cttgtgcttg cctagcttct tattattatt acaaccacaa gcttgtcgac     540
ttcccgaccg aaacagatcc caagatcgat gtccagatcc cgtgcatgcc tgtcttgaaa     600
cacgacgaga tcccttcttt catccatcct ttttcacctt attcgggttt aagagaagtg     660
atcattgatc agatcaaacg tcttcacaag cctttcgctg ttctcatcga tacttttctac     720 tccttggaga aagatatcat cgaccacatg acaaacctct ctcgcaccgg ctttgtcaga     780
ccgctcggac cgctttacaa aatggccaaa acgttgattt gtgatgacat caaggagat     840 atgtctgaga cgagggatga ctgcatggag tggttagact cgcagcctgt ttcgtccgtt     900
gtttacatct catttggtac cgtggcttac gtgacacaag aacagatcag cgagattgcg     960
ttaggcgttt taaacgctga cgtttcgttc ttgtgggtga taagacaaca agaactaggt    1020
gtaaacaaag agcgacatgt tctgcctgaa gaactcaaag ggaaaggtaa agtcattgaa    1080
tggtgttcac aagagaaagt cttagctcat ccttctgtgg tttgtttcgt gactcattgt    1140
ggatggaact caacgatgga agctttgtct agtggagtcc caacggtctg ttttcctcag    1200
tggggagatc aagtcaccga cgctgcttac atgatcgacg tgttcaagac gggagtgagg    1260
cttagccgtg gagagacgga ggagagggtg gtgcctaggg aggaagtagc ggagaggctg    1320
agagaagtta cgaaaggaga gaaagcgacg gagctgaaga agaatgcttt aaaatggaag    1380
```

-continued

```
gaggaggcgg aagcggccgt ggctcgcggt ggttcgtcgg atcggaatct tgatgagttt    1440
gtggaaaagt tgggcgtgaa acctgtggct aaacagaacg gaagtctcaa tcaaaacgga    1500
agtattcaaa aacttttatt gcaaaagtca taaatgtgtt ttgtattatc tgttgtttgt    1560
tttctgcaaa tcctgataat tgtgtttgtt tgtatgctcc ctccgttctt tgttctcgtt    1620
ttttttttgt atgggtttgg ggagactagt tatccttctt gaataaatgt tagatcacga    1680
cttgtgttct taagattaaa aaaaaaaaaa aaaaa                               1715

<210> SEQ ID NO 2
<211> LENGTH: 1715
<212> TYPE: DNA
<213> ORGANISM: Brassica napus
<220> FEATURE:
<221> NAME/KEY: CDS
<222> LOCATION: (40)..(1533)

<400> SEQUENCE: 2
gaaaaacaga gcacacagaa gagaacccct ttttgaagg atg gaa cta tca tct      54
                                           Met Glu Leu Ser Ser
                                             1               5 tct cct tta cct cct cat gtt atg ctt gta tcc ttc cca gga caa ggc    102
Ser Pro Leu Pro Pro His Val Met Leu Val Ser Phe Pro Gly Gln Gly
             10                  15                  20 cac gtt aat cca ctt ctt cgt ctc ggc aag ctc tta gct tcg aag ggt    150
His Val Asn Pro Leu Leu Arg Leu Gly Lys Leu Leu Ala Ser Lys Gly
         25                  30                  35 tta ctc gtc act ttt gtc acc aca gaa tca tgg ggc aaa aag atg cga    198
Leu Leu Val Thr Phe Val Thr Thr Glu Ser Trp Gly Lys Lys Met Arg
     40                  45                  50 acc gcc aac aag att caa gac cga gcc ctc aaa cct atc ggt aaa ggt    246
Thr Ala Asn Lys Ile Gln Asp Arg Ala Leu Lys Pro Ile Gly Lys Gly
 55                  60                  65 tat ctc cgg ttc gat ttc ttc aac gat ggg ctc cct gaa gac gac gat    294
Tyr Leu Arg Phe Asp Phe Phe Asn Asp Gly Leu Pro Glu Asp Asp Asp
 70                  75                  80                  85 gca agc aga acc aac tta acc atc ctc cga cca caa ctc gag ctg gtc    342
Ala Ser Arg Thr Asn Leu Thr Ile Leu Arg Pro Gln Leu Glu Leu Val
                 90                  95                 100 gga caa caa gag atc aaa aac ctc gtg aaa cgt tac aag gaa gtg atg    390
Gly Gln Gln Glu Ile Lys Asn Leu Val Lys Arg Tyr Lys Glu Val Met
             105                 110                 115 aaa cag ccc gtg acg tgt ctc atc aac aac cct ttc gtc tct tgg gtc    438
Lys Gln Pro Val Thr Cys Leu Ile Asn Asn Pro Phe Val Ser Trp Val
         120                 125                 130 tgt gac gta gcc gaa gat ctt caa atc ccc tgt gct gtt ctc tgg gtc    486
Cys Asp Val Ala Glu Asp Leu Gln Ile Pro Cys Ala Val Leu Trp Val
     135                 140                 145 cag tct tgt gct tgc cta gct tct tat tat tat tac aac cac aag ctt    534
Gln Ser Cys Ala Cys Leu Ala Ser Tyr Tyr Tyr Tyr Asn His Lys Leu
 150                 155                 160                 165 gtc gac ttc ccg acc gaa aca gat ccc aag atc gat gtc cag atc ccg    582
Val Asp Phe Pro Thr Glu Thr Asp Pro Lys Ile Asp Val Gln Ile Pro
                 170                 175                 180 tgc atg cct gtc ttg aaa cac gac gag atc cct tct ttc atc cat cct    630
Cys Met Pro Val Leu Lys His Asp Glu Ile Pro Ser Phe Ile His Pro
             185                 190                 195 ttt tca cct tat tcg ggt tta aga gaa gtg atc att gat cag atc aaa    678
Phe Ser Pro Tyr Ser Gly Leu Arg Glu Val Ile Ile Asp Gln Ile Lys
         200                 205                 210
```

```
cgt ctt cac aag cct ttc gct gtt ctc atc gat act ttc tac tcc ttg      726
Arg Leu His Lys Pro Phe Ala Val Leu Ile Asp Thr Phe Tyr Ser Leu
    215                 220                 225 gag aaa gat atc atc gac cac atg aca aac ctc tct cgc acc ggc ttt      774
Glu Lys Asp Ile Ile Asp His Met Thr Asn Leu Ser Arg Thr Gly Phe
230                 235                 240                 245 gtc aga ccg ctc gga ccg ctt tac aaa atg gcc aaa acg ttg att tgt      822
Val Arg Pro Leu Gly Pro Leu Tyr Lys Met Ala Lys Thr Leu Ile Cys
                250                 255                 260 gat gac atc aaa gga gat atg tct gag acg agg gat gac tgc atg gag      870
Asp Asp Ile Lys Gly Asp Met Ser Glu Thr Arg Asp Asp Cys Met Glu
            265                 270                 275 tgg tta gac tcg cag cct gtt tcg tcc gtt gtt tac atc tca ttt ggt      918
Trp Leu Asp Ser Gln Pro Val Ser Ser Val Val Tyr Ile Ser Phe Gly
        280                 285                 290 acc gtg gct tac gtg aca caa gaa cag atc agc gag att gcg tta ggc      966
Thr Val Ala Tyr Val Thr Gln Glu Gln Ile Ser Glu Ile Ala Leu Gly
    295                 300                 305 gtt tta aac gct gac gtt tcg ttc ttg tgg gtg ata aga caa caa gaa     1014
Val Leu Asn Ala Asp Val Ser Phe Leu Trp Val Ile Arg Gln Gln Glu
310                 315                 320                 325 cta ggt gta aac aaa gag cga cat gtt ctg cct gaa gaa ctc aaa ggg     1062
Leu Gly Val Asn Lys Glu Arg His Val Leu Pro Glu Glu Leu Lys Gly
                330                 335                 340 aaa ggt aaa gtc att gaa tgg tgt tca caa gag aaa gtc tta gct cat     1110
Lys Gly Lys Val Ile Glu Trp Cys Ser Gln Glu Lys Val Leu Ala His
            345                 350                 355 cct tct gtg gtt tgt ttc gtg act cat tgt gga tgg aac tca acg atg     1158
Pro Ser Val Val Cys Phe Val Thr His Cys Gly Trp Asn Ser Thr Met
        360                 365                 370 gaa gct ttg tct agt gga gtc cca acg gtc tgt ttt cct cag tgg gga     1206
Glu Ala Leu Ser Ser Gly Val Pro Thr Val Cys Phe Pro Gln Trp Gly
    375                 380                 385 gat caa gtc acc gac gct gct tac atg atc gac gtg ttc aag acg gga     1254
Asp Gln Val Thr Asp Ala Ala Tyr Met Ile Asp Val Phe Lys Thr Gly
390                 395                 400                 405 gtg agg ctt agc cgt gga gag acg gag gag agg gtg gtg cct agg gag     1302
Val Arg Leu Ser Arg Gly Glu Thr Glu Glu Arg Val Val Pro Arg Glu
                410                 415                 420 gaa gta gcg gag agg ctg aga gaa gtt acg aaa gga gag aaa gcg acg     1350
Glu Val Ala Glu Arg Leu Arg Glu Val Thr Lys Gly Glu Lys Ala Thr
            425                 430                 435 gag ctg aag aag aat gct tta aaa tgg aag gag gag gcg gaa gcg gcc     1398
Glu Leu Lys Lys Asn Ala Leu Lys Trp Lys Glu Glu Ala Glu Ala Ala
        440                 445                 450 gtg gct cgc ggt ggt tcg tcg gat cgg aat ctt gat gag ttt gtg gaa     1446
Val Ala Arg Gly Gly Ser Ser Asp Arg Asn Leu Asp Glu Phe Val Glu
    455                 460                 465 aag ttg ggc gtg aaa cct gtg gct aaa cag aac gga agt ctc aat caa     1494
Lys Leu Gly Val Lys Pro Val Ala Lys Gln Asn Gly Ser Leu Asn Gln
470                 475                 480                 485 aac gga agt att caa aaa ctt tta ttg caa aag tca taa atgtgttttg     1543
Asn Gly Ser Ile Gln Lys Leu Leu Leu Gln Lys Ser
                490                 495 tattatctgt tgtttgtttt ctgcaaatcc tgataattgt gtttgtttgt atgctccctc   1603
cgttctttgt tctcgttttt tttttgtatg ggtttgggga gactagttat ccttcttgaa   1663
taaatgttag atcacgactt gtgttcttaa gattaaaaaa aaaaaaaaaa aa           1715
```

```
<210> SEQ ID NO 3
<211> LENGTH: 497
<212> TYPE: PRT
<213> ORGANISM: Brassica napus

<400> SEQUENCE: 3

Met Glu Leu Ser Ser Pro Leu Pro His Val Met Leu Val Ser
 1               5                  10                  15

Phe Pro Gly Gln Gly His Val Asn Pro Leu Leu Arg Leu Gly Lys Leu
                20                  25                  30

Leu Ala Ser Lys Gly Leu Leu Val Thr Phe Val Thr Glu Ser Trp
            35                  40                  45

Gly Lys Lys Met Arg Thr Ala Asn Lys Ile Gln Asp Arg Ala Leu Lys
        50                  55                  60

Pro Ile Gly Lys Gly Tyr Leu Arg Phe Asp Phe Asn Asp Gly Leu
 65                  70                  75                  80

Pro Glu Asp Asp Asp Ala Ser Arg Thr Asn Leu Thr Ile Leu Arg Pro
                85                  90                  95

Gln Leu Glu Leu Val Gly Gln Gln Glu Ile Lys Asn Leu Val Lys Arg
            100                 105                 110

Tyr Lys Glu Val Met Lys Gln Pro Val Thr Cys Leu Ile Asn Asn Pro
        115                 120                 125

Phe Val Ser Trp Val Cys Asp Val Ala Glu Asp Leu Gln Ile Pro Cys
    130                 135                 140

Ala Val Leu Trp Val Gln Ser Cys Ala Cys Leu Ala Ser Tyr Tyr Tyr
145                 150                 155                 160

Tyr Asn His Lys Leu Val Asp Phe Pro Thr Glu Thr Asp Pro Lys Ile
                165                 170                 175

Asp Val Gln Ile Pro Cys Met Pro Val Leu Lys His Asp Glu Ile Pro
            180                 185                 190

Ser Phe Ile His Pro Phe Ser Pro Tyr Ser Gly Leu Arg Glu Val Ile
        195                 200                 205

Ile Asp Gln Ile Lys Arg Leu His Lys Pro Phe Ala Val Leu Ile Asp
    210                 215                 220

Thr Phe Tyr Ser Leu Glu Lys Asp Ile Ile Asp His Met Thr Asn Leu
225                 230                 235                 240

Ser Arg Thr Gly Phe Val Arg Pro Leu Gly Pro Leu Tyr Lys Met Ala
                245                 250                 255

Lys Thr Leu Ile Cys Asp Asp Ile Lys Gly Asp Met Ser Glu Thr Arg
            260                 265                 270

Asp Asp Cys Met Glu Trp Leu Asp Ser Gln Pro Val Ser Ser Val Val
        275                 280                 285

Tyr Ile Ser Phe Gly Thr Val Ala Tyr Val Thr Gln Glu Gln Ile Ser
    290                 295                 300

Glu Ile Ala Leu Gly Val Leu Asn Ala Asp Val Ser Phe Leu Trp Val
305                 310                 315                 320

Ile Arg Gln Gln Glu Leu Gly Val Asn Lys Glu Arg His Val Leu Pro
                325                 330                 335

Glu Glu Leu Lys Gly Lys Gly Lys Val Ile Glu Trp Cys Ser Gln Glu
            340                 345                 350

Lys Val Leu Ala His Pro Ser Val Val Cys Phe Val Thr His Cys Gly
        355                 360                 365

Trp Asn Ser Thr Met Glu Ala Leu Ser Ser Gly Val Pro Thr Val Cys
    370                 375                 380
```

```
Phe Pro Gln Trp Gly Asp Gln Val Thr Asp Ala Ala Tyr Met Ile Asp
385                 390                 395                 400

Val Phe Lys Thr Gly Val Arg Leu Ser Arg Gly Glu Thr Glu Glu Arg
                405                 410                 415

Val Val Pro Arg Glu Glu Val Ala Glu Arg Leu Arg Glu Val Thr Lys
            420                 425                 430

Gly Glu Lys Ala Thr Glu Leu Lys Lys Asn Ala Leu Lys Trp Lys Glu
        435                 440                 445

Glu Ala Glu Ala Ala Val Ala Arg Gly Gly Ser Ser Asp Arg Asn Leu
    450                 455                 460

Asp Glu Phe Val Glu Lys Leu Gly Val Lys Pro Val Ala Lys Gln Asn
465                 470                 475                 480

Gly Ser Leu Asn Gln Asn Gly Ser Ile Gln Lys Leu Leu Leu Gln Lys
            485                 490                 495

Ser
```

METHOD FOR INFLUENCING THE CONTENT OF SINAPINE IN TRANSGENIC PLANT CELLS AND IN PLANTS

The invention relates to a method for influencing the content of sinapine in transgenic plant cells and plants. In particular, the invention relates to the inhibition of the enzymatic activity of a UDP-glucose: sinapate glucose transferase (SGT) in transgenic plant cells. The invention also relates to nucleic acid molecules containing a DNA sequence which codes for a protein having the enzymatic activity of an SGT. The invention furthermore relates to transgenic plants and plant cells, comprising a nucleic acid molecule according to the invention, and due to that they contain a reduced content of sinapine in comparison with wild-type plants or cells, and the agricultural products and propagating material of the transgenic plants.

In the last 15 years, the production of plant oils has greatly increased throughout the world, and the proportion of rape oil has increased more than that of other oil types. Rape is mostly cultivated in order to obtain high quality oils for the food industry. Extracted rape oil is however increasingly used in other branches of industry. Rape oil is also becoming increasingly interesting as a renewable raw material to replace the limited resources of fossil fuels.

Large quantities of rape groats or meal remain as residue after the isolation of the oil, and this is used as a valuable protein-rich fodder. This has restricted use in animal nutrition. The protein content of the seeds of rape meal is about 20%, which is comparable to that of soy meal. The proportion of essential amino acids is also about the same as in soy meal, so that the rape protein is comparable to soy protein as far as nutritional value is concerned. There is thus enormous interest in making rape protein also available as food for human consumption.

The use of rape meal in animal nutrition and the use of rape proteins in human nutrition are however restricted by the high proportion of antinutritive components. Glucosinolates (D. W. Griffiths, J. Hortic (1998) *Sci. & Biotechnol.* 73:1-18) were initially regarded as the most important and limiting antinutritive factors, but have been largely reduced by the introduction of new varieties of rape, such as Canola, and can be fully eliminated by breeding processes.

Phenolic components are another important group of substances with antinutritive properties (A. Bouchereau et al. (1991), *Phytochemistry* 30:1873-1881). The content of phenols in rape meal is about thirty times as high as in soy meal. Phenolic compounds are implicated in the dark colour, the bitter taste, the unpleasant smell and the astringent properties of the rape meal (R. Blair und D. R. Reichert (1984), *J. Sci. Food Agric.* 35: 29-35). In rapeseeds, soluble phenolic compounds mainly accumulate in the cotyledons of the embryos. The predominant component is sinapoylcholine (sinapine), which is present with a content of 1 to 2% in rape meal.

Sinapine has also been connected with a fishy smell in the eggs of laying hens after they have been fed with rape seed. This smell is due to the accumulation of triethylamine in the eggs (R. G. Fenwick et al. (1984), *J. Sci. Food Agric.* 35:757-761). It is postulated that the rapeseed tannins inhibit triethylamine oxidase in hens by complex formation and thus prevent the formation of triethylamine oxide, which is odourless.

As mentioned above, the accumulation of phenolic choline esters in the cotyledons of the seed embryos is a typical characteristic of many Brassicaceae (Cruciferae). Sinapoylcholine (sinapine) can make up 1 to 2% of dry weight of the seeds and is therefore by far the most important member of this class of substances (K. Krygier et al. (1982), *J. Food Chem.* 30:661-663); A. Bouchereau et al., vide supra). Other esters of hydroxycinnamic acid are only present in very small amounts (T. W. Fenton et al. (1980), *J. Food Sci.* 45:1703-1705). There have as yet been few studies on the biochemical mechanisms underlying the storage of sinapines in the seeds. It has nevertheless been established that the vegetative parts of the plant are not a possible source of the sinapine acid in the seeds, since they are not detectable there. Thus Bopp and Luedicke (*Z. Naturforsch.* 1980, 35c: 539-543) demonstrated that radioactive $^{14}$C is incorporated into sinapine after feeding immature mustard embryos with $^{14}$C-phenylalanine. It can be concluded from this that all enzymes for the biosynthesis of hydroxycinnamic acid, from phenylalanine-ammonia lyase (PAL) to sinapine synthase, are active in the seed embryos.

The catabolism of sinapine during seed germination and seedling development has also been well examined in representatives of the Brassicaceae (A. Tzagoloff (1963), *Plant. Physiol.* 38:202-206; M. Bopp and W. Luedicke (1975), *Z. Naturforsch.* 30c:663-667; D. Strack (1977), *Z. Pflanzenphysiol.* 84:139-145). In germinating seeds, sinapine is hydrolysed by an sinapine esterase (G. Nurmann and D. Strack (1979), *Z. Naturforsch.* 34c:715-720; D. Strack et al. (1980), *Z. Naturforsch.* 35c:963-966) and serves as a source of choline for the membrane lipids of the young germinal plants (D. Strack (1981), *Z. Naturforsch.* 36c:215-221). Sinapic acid is converted into sinapoylmalate via sinapoylglucose as intermediate (D. Strack (1977)).

It is not yet totally clear whether sinapine is of essential importance as a reserve substance. Chapple et al. (1992, *The Plant Cell* 4:1413-1424) examined mutants of Arabidopsis having a greatly reduced sinapine content (5% of the wild-type). These mutants accumulate predominantly free choline instead of the choline ester. The germination rate and the growth of the mutants were comparable to those of the wild-type. It can be concluded from these results that sinapine is not an essential component of the seed for seed germination or seedling development.

An object of the present invention is therefore to provide transgenic plants, which have a reduced content of sinapine in comparison with their wild-type form, and which are therefore more suitable in order to obtain proteins for nutritional purposes.

The development of rape varieties having low sinapine content by classical breeding protocols has as yet been not very successful. Although some of the varieties used exhibit clear differences in the content of phenolic secondary metabolites and in the sinapine concentration, selection for low sinapine content requires a great deal of time and is poorly reproducible.

It is therefore a further object of the present invention to reduce the sinapine content in plants by genetic suppression of the enzyme activities of the sinapine biosynthetic pathway.

Starting from sinapic acid which is formed in immature seeds by the hydroxycinnamic acid biosynthetic pathway, two enzymes are needed for the formation of sinapine, namely UDP-glucose: sinapate glucosyltransferase (SGT) (Nurmann und Strack (1981), supra) and sinapoylglucose: choline sinapoyltransferase (sinapine synthase; SCT) (Strack et al., (1983), supra):

It is therefore another object of the present invention to reduce or to completely block the endogenous SGT activity in transgenic plants, particularly in transgenic oil seeds and more particularly in transgenic rape plants.

The gene sequences coding for SGT or SCT are unknown. SCT was detected in 44 members of the Brassicaceae and a correlation was found between SCT activity and sinapine content (J. Regenbrecht and D. Strack (1985), *Phytochemistry* 24:407-410). Purification of the SGT from *Brassica napus* seedlings has recently been described by Wang and Ellis (*Phytochemistry* (1998) 49:307-318). Partial purification of this enzyme has also been described (H.-P. Mock and D. Strack (1993), *Phytochemistry* 92: 575-579). There are however as yet no useful sequence data on SCT or SGT.

The present invention therefore also has the object of providing methods of influencing the sinapine content in plants and of providing recombinant DNA molecules containing a DNA sequence, which can be used for the manipulation of the sinapine content. The above mentioned and other objects of the invention were solved by providing the embodiments described in the claims.

In the context of the present invention, a DNA sequence is disclosed for the first time which codes for a protein having the enzymatic activity of an SGT. The sequence is preferably derived from *Brassica*, most preferably from *Brassica napus*.

By providing the DNA sequences according to the invention, the SGT can be effectively inhibited, for example, by transfer of anti-sense or sense or co-suppression constructs of the DNA sequences according to the invention, which leads to an interruption of the production of sinapine in the seeds. The "double strength RNA interference" technique, also known as "post-transcriptional gene silencing" (PTGS) is moreover especially suitable for the suppression of the SGT activity in transgenic plants. In contrast to the classical "anti-sense" technique, the "double strength RNA interference" method is based on the formation of a stable RNA double strand of the gene, which is to be suppressed in the plant cell. This method leads to suppression of the specific target gene, and is at least as efficient as that achieved with the normal "anti-sense" technique. In order to achieve optimal double strand formation, it is recommended to incorporate an intron between the sense and anti-sense fragments.

The observation that the sinapine content can be effectively reduced by inhibiting the SGT can be used in an ideal manner for the production of low sinapine or sinapine-free plant transformants, which are suitable for the isolation of proteins to be used as food. The basis for the production of such useful plants is the availability of suitable transformation systems. A broad spectrum of transformation methods have been developed and established for this purpose in the last two decades. These techniques include the transformation of plant cells with T-DNA using *Agrobacterium tumefaciens* or *Agrobacterium rhizogenes* as the transforming agent, the fusion of protoplasts, the direct gene transfer of isolated DNA into protoplasts, the injection and electroporation of DNA into plant cells, the introduction of DNA by biolistic methods and other possibilities.

Apart from providing the SGT-DNA sequences according to the invention, the person skilled in the art may identify other DNA sequences that code for SGT in other organisms, using conventional techniques of molecular biology, and employ these in the context of the present invention. For example, the person skilled in the art may derive suitable hybridisation probes from the SGT sequences according to the invention and use these for the screening of cDNA and/or genomic libraries of the desired organism from which a new SGT gene is to be isolated. For this purpose, the person skilled in the art may use conventional hybridisation, cloning and sequencing methods, which are well known and established in every laboratory working in the field of genetic or biological engineering (see for example Sambrook et al. (1989) Molecular Cloning: A Laboratory Manual, 2. Edition, Cold Spring Harbour Laboratory Press, Cold Spring Harbour, N.Y.). On the basis of the sequences according to the invention, it is also of course possible for the person skilled in the art to synthesise and to use suitable oligonucleotide primers for PCR amplifications of SGT sequences.

In an essential embodiment of the present invention, the inventive DNA sequence, which codes for an SGT is present in the anti-sense orientation. Using the anti-sense technique, the endogenous SGT gene or genes may be intentionally inactivated, by ligating the DNA sequence according to the invention in an "inverted", i.e. in anti-sense orientation to a vector. The RNA that is synthesised throughout transcription of such an anti-sense gene is complementary to the RNA of the normal gene and may thus prevent synthesis of the SGT protein product, as a result of hybridisation between the native and the anti-sense RNA.

Alternatively, the endogenous SGT expression can be inhibited by a co-suppression construct of the nucleic acid molecule according to the invention. In co-suppression, a pre-active gene is inactivated by additionally introducing identical copies of this gene. This inactivation is presumably due to an RNA-dependent mechanism, involving RNA-directed RNA polymerase.

As mentioned above, another preferred approach to suppression is the use of the PTGS method, which is based on the formation of a stable RNA double strand of the gene to be suppressed, i.e. of the endogenous SGT gene of the plant cell.

It is clear to the person skilled in the art that it is not absolutely essential to use the complete DNA sequence, which codes for the SGT in order to achieve a suppression effect that results in the inhibition of endogenous SGT activity. The invention therefore also relates to fragments of the DNA sequences according to the invention, whose use results in reduced activity of the target SGT enzyme within an anti-sense, sense or PTGS construct. In the context of this invention, these fragments could also be called "anti-sense, suppression or PTGS-active" DNA fragments, i.e. their transfer in the form of a suitable construct causes a reduction in endogenous SGT enzyme activity.

The person skilled in the art may easily transfer different fragments using conventional techniques in order to establish which lengths or segments of the total SGT coding sequence are necessary for the fragment to be suitable for the inhibition of endogenous enzyme activity.

The only further requirement for the application of the present invention is the presence of suitable regulatory sequences, which control the transcription of an operatively linked SGT-DNA sequence in the seeds of the transformed plants. Here too, the person skilled in the art may use suitable sequences according to the state of the art without any problems, or can himself isolate seed-specific promoter sequences. Examples of regulatory sequences, which are particularly suitable for the seed-specific transcription of the sequences according to the invention or fragments thereof, are the USP promoter from *Vicia faba* (Bäumlein H. et al. (1991) *Mol. Gen. Genet.* 225:459-467; Bäumlein H. et al. (1991) *Mol. Gen. Genet.* 225:121-128), the LeB4 promoter from *Vicia faba* (Nagy I. (1990) "Studies on the Expression and Regulation of the Seed-Specific Genes of *Vicia faba*" Dissertation, University of Halle) and the DC3 promoter from *Daucus carota* (Steffens W. S. et al. (1990) *Dev. Genet.* 11(1):65-76). The napin promoter is used in another preferred embodiment.

Particularly preferred regulatory sequences are those of the USP or LeB4 promoter. These seed-specific promoters can be used either for anti-sense, sense or PTGS constructs, to achieve changes in the sinapine biosynthetic pathway, with the aim of reducing the level of sinapine in the seeds.

Although seed-specific expression is preferred, any sort of regulatory sequence which guarantees transcription in plant cells is possible for the expression of the DNA sequence according to the invention in plant cells. This includes any promoter that is active in plant cells. The promoter can be selected so that the expression is constitutive or is only expressed in seed tissue at specific times in the development of the plant and/or at times determined by external influences, which may be either biotic or abiotic stimuli (induced gene expression). The promoter may either be homologous or heterologous to the plant to be transformed. If a constitutive promoter is used, cell-specific or tissue-specific expression can also be achieved by inhibiting the gene expression in the cells or in the tissues where it is not desired, for example by expressing antibodies which bind the gene product and thus suppress its enzyme activity, or by suitable inhibitors.

The person skilled in the art may use seed-specific genes or promoters known in the art, in particular from relevant scientific journals and gene databases. In addition, the person skilled in the art is capable of isolating other suitable promoters using routine methods. Thus the person skilled in the art can identify seed-specific regulatory nucleic acid elements using current methods in molecular biology, such as hybridisation experiments or DNA-protein binding studies. For example, as a first step the total PolyA$^+$-RNA is isolated from the seed tissue of the desired organism from which the regulatory sequences are to be isolated; and a cDNA library is then set up. As a second step, cDNA clones based on polyA$^+$-RNA molecules from non-seed tissue are used to identify by hybridisation those clones from the first library whose corresponding polyA$^+$-RNA molecules only accumulate in seed tissue. These thus identified cDNAs are then used to isolate promoters that have seed-specific regulatory elements. Further methods based on PCR for the isolation of suitable seed-specific promoters are also available to the person skilled in the art.

Optionally, transcription or termination sequences are also present that provide for correct transcription termination and may provide for the addition of a polyA tail to the transcript, to which a function in the stabilisation of transcripts is attributed. Such elements are described in the literature and are interchangeable in any order.

Finally, chimeric gene constructs are prepared, in which DNA sequences coding for SGT are under the control of regulatory sequences that guarantee seed-specific transcription, using conventional cloning methods (see for example Sambrook et al. (1989), supra). The present invention therefore relates to a recombinant nucleic acid molecule, comprising:

a) regulatory sequences of a promoter that is active in plants, especially in plant seeds;
b) operatively linked thereto a DNA sequence, which encodes a protein having the enzymatic activity of an SGT, or a fragment of the DNA sequence sufficient to suppress endogenous SGT enzyme activity, and
c) optionally, operatively linked thereto regulatory sequences, which may serve as transcription, termination and/or polyadenylation signals in plant cells.

As explained above, operatively linking the SGT DNA sequence (b) to the regulatory sequences (a) may be in sense or anti-sense orientation of the SGT-DNA sequence.

The DNA sequence encoding a protein having the enzymatic activity of an SGT may be isolated from natural sources or synthesised by known methods. The DNA sequence according to the invention is preferably derived from *Brassica*, particularly from *Brassica napus*.

It is possible to prepare or produce desired constructs for the transformation of plants using current molecular biological techniques (see for example Sambrook et al. (1989), supra). The cloning, mutagenesis, sequence analysis, restriction analysis and other biochemical and molecular biological methods usually used for gene technological manipulation in prokaryotic cells are well known to the person skilled in the art. It is thus not only possible to produce suitable chimeric gene constructs with the desired fusion of promoter and the SGT DNA sequence. In fact, the person skilled in the art can, if desired, use routine techniques to introduce mutations or deletions of various types into the DNA sequence coding for SGT.

In a preferred embodiment, the DNA sequence that codes for a protein having the enzymatic activity of an SGT is selected from the group consisting of:

a) DNA sequences comprising a nucleotide sequence encoding the amino acid sequence given in SEQ ID No. 3 or fragments thereof; p1 b) DNA sequences comprising the nucleotide sequence given in SEQ ID No. 1 or parts thereof;
c) DNA sequences comprising a nucleotide sequence hybridising with a complementary strand of the nucleotide sequence of a) or b), or comprising parts of this nucleotide sequence;
d) DNA sequences comprising a nucleotide sequence which is degenerate to a nucleotide sequence of c), or parts of this nucleotide sequence.
e) DNA sequences which are a derivative, an analogue or a fragment of a nucleotide sequence of a), b), c) or d).

In the context of the present invention the term "hybridisation" means a hybridisation under conventional hybridisation conditions, preferably under stringent conditions, as described for example in Sambrook et al. (1989, supra). Suitable stringent conditions include salt solutions of about 0.9 molar at temperatures of 35° C. to 65° C. Stringent hybridisation conditions preferably comprise the following conditions:

| | |
|---|---|
| Hybridisation buffer: | 7% SDS |
| | 250 mM NaCl |
| | 250 mM K-phosphate buffer pH 7.0 |
| | 1 mM EDTA |
| Hybridisation temperature: | 58° C. to 60° C. |
| Hybridisation time: | overnight |
| Washing buffer: | I 2 × SSC 0.1% SDS |
| | II 0.2 × SSC 0.1% SDS |
| Washing temperature and time: | each 2 × 30 min at 55° C. to 60° C. |

DNA sequences hybridising with DNA sequences that code for a protein having the enzymatic activity of an SGT can, for instance be isolated from genomic or cDNA libraries. Such DNA sequences can be identified and isolated, for example by using DNA sequences, which either exactly or essentially have one of the afore-mentioned SGT coding nucleotide sequences or parts of these sequences, or the reverse complements of these DNA sequences, for instance by hybridisation according to standard methods (see for example Sambrook et al. (1989), supra). Fragments used as hybridisation probe can also be synthetic fragments which have been produced using conventional synthesis techniques and whose sequence substantially corresponds to one of the afore-mentioned DNA sequences for SGT or a part of one of these sequences. The DNA sequences coding for a protein having the enzymatic activity of an SGT also comprise DNA sequences whose nucleotide sequence is degenerate to one of the DNA sequences described above.

The DNA sequences according to the invention also comprise fragments, derivatives and allelic variants of the DNA sequences described above, which code for a protein having the enzymatic activity of an SGT. The term "derivative" means in this context that the sequences differ from the DNA sequences described above at one or more positions, but have a high degree of homology to these sequences. Homology here means a sequence identity of at least 40%, particularly an identity of at least 60% or 70%, preferably of at least 80%, 82%, 84%, 86% or 88%, and particularly preferably of at least 90%, 92%, 94%, 96% or 98%. Variations from the DNA sequences described above may be caused, for example, by deletion, substitution, insertion or recombination.

The DNA sequences, which are homologous to the above-mentioned sequences and which are derivatives of these sequences are generally variations of these sequences, which represent modifications having the same biological function. These variations may be both naturally occurring variations, for example sequences from other organisms, or mutations, wherein these mutations may have occurred naturally or have been introduced by targeted mutagenesis. Moreover, the variations can further comprise synthetic sequences. The allelic variants may be naturally occurring variants or synthetic variants or variants created by recombinant DNA techniques.

In a more preferred embodiment the described DNA sequence coding for an SGT originates from *Brassica napus* (as given in SEQ ID No. 1).

The enzymes encoded by the DNA sequences according to the invention have an amino acid sequence corresponding to the sequence given in SEQ ID No. 3 in at least 30% or 40% of the amino acids, in particular in at least 50%, 60% or 70%, preferably in 80%, 82%, 84%, 86% or 88% and especially preferred in at least 90%, 92%, 94%, 96% or 98% of the amino acids.

The invention also relates to vectors and micro-organisms which contain the nucleic acid molecules according to the invention, and whose usage makes it possible to produce plant cells and plants having a reduced content of sinapine compared to wild-type plant cells or plants. The vectors especially include plasmids, cosmids, viruses, bacteriophages and other vectors common in gene technology. The micro-organisms are primarily bacteria, viruses, fungi, yeasts and algae.

In addition, the present invention provides a recombinant protein having the enzymatic activity of an SGT from *Brassica*, in particular a recombinant protein having the amino acid sequence given in SEQ ID No. 3.

The invention also relates to a method for producing plants or plant cells having lower sinapine content compared to wild-type plants or plant cells, comprising the following steps:
 a) Production of a recombinant nucleic acid molecule that comprises the following sequences:
  regulatory sequences of a promoter that is active in plants,
  operatively linked thereto a DNA sequence, which codes for a protein having the enzymatic activity of an SGT, and
  optionally, operatively linked thereto regulatory sequences, which can serve as transcription, termination and/or polyadenylation signals in plant cells,
 b) Transfer of the nucleic acid molecule from a) to plant cells, and
 c) Optionally, regeneration of intact plants from the transformed plant cells.

In a particularly preferred embodiment of the present invention, the DNA sequence that codes for a protein having the enzymatic activity of an SGT is present as an anti-sense-, sense- or co-suppression construct or as a PTGS construct, in order to inhibit or totally suppress the expression of the SGT in the transformed plant or plant cell, thus effectuating a reduction in the sinapine content in the transformed plants.

A further aspect of the present invention is that inhibition of the biosynthesis of sinapine increases the bioavailability of coumaric acid, which is an intermediate in sinapine biosynthesis. Coumaric acid is needed for the biosynthesis of resveratrol, which is of nutritional significance. Inhibition of sinapine biosynthesis also leads to the accumulation of free choline. It is therefore a further advantage of the present invention that the availability of choline for lecithin biosynthesis is increased, which leads in case of transformed oil seeds to an increase in the content of fatty acids, for instance of palmitic acid, stearic acid, palmitoleic acid, oleic acid, linoleic acid and linolenic acid.

The invention also relates to plant cells containing the nucleic acid molecules according to the invention which encode a protein having the enzymatic activity of an SGT. The invention also relates to agricultural products and propagating material from transgenic plants and the transgenic plants themselves, which contain a nucleic acid molecule according to the invention. As the result of the introduction of a DNA sequence encoding an SGT, preferably in anti-sense orientation or as co-suppression construct, the transgenic plants of the present invention exhibit a reduced sinapine content.

In a further aspect of the present invention plant protein may be obtained from plants transformed with an SGT-DNA sequence according to the invention, wherein the protein has a reduced content of sinapine compared to wild-type plants and which can therefore be used advantageously for nutritional purposes.

In a preferred embodiment of the present invention, the plant protein having reduced sinapine content is isolated from rapeseed that has been transformed with an SGT-DNA sequence of the present invention in anti-sense orientation or as co-suppression construct.

In order to prepare the introduction of foreign genes into higher plants or their cells a large number of cloning vectors are available which contain a replication signal for *E. coli* and a marker gene for selecting transformed bacterial cells. Examples of such vectors include pBR322, the pUC series, the M13mp series, pACYC184 and the like. The desired sequence can be introduced into the vector at a suitable restriction site. The plasmid obtained is then used for the transformation of *E. coli* cells. Transformed *E. coli* cells are cultivated in a suitable medium, then harvested and lysed and the plasmid is recovered. Restriction analyses, gel electrophoresis and other biochemical-molecular biological methods are generally used as analytic methods to characterise the plasmid DNA so obtained. After each manipulation the plasmid DNA may be cleaved and the thus obtained DNA fragments can be linked to other DNA sequences.

A plurality of techniques is available for introducing DNA into a plant host cell and the person skilled in the art will not have any difficulties in selecting a suitable method in each case. As already mentioned above, these techniques comprise the transformation of plant cells with T-DNA using *Agrobacterium tumefaciens* or *Agrobacterium rhizogenes* as the transforming agent, the fusion of protoplasts, injection, electroporation or direct gene transfer of isolated DNA in protoplasts, introduction of DNA using the biolistic method and other possibilities which have been well established for several years and which belong to the standard repertoire of the person skilled in the art in plant molecular biology or plant biotechnology.

For the injection and electroporation of DNA into plant cells, the plasmids used do not have to fulfil any particular requirements per se. The same applies to direct gene transfer. Simple plasmids such as pUC derivatives, can be used. However, if entire plants are to be regenerated from these transformed cells, the presence of a selectable marker gene is recommended. The person skilled in the art is familiar with current selection markers and does not have a problem in selecting a suitable marker.

Depending on the method of introduction of the desired genes into the plant cell, further DNA sequences may be required. If, for example, the Ti or Ri plasmids are used for the transformation of the plant cell, at least the right border, although more often both the right and the left border of the T-DNA contained in the Ti or Ri plasmid must be linked to the genes to be inserted as flanking region. If agrobacteria are used for the transformation, the DNA to be integrated must be cloned into special plasmids and specifically either into an intermediate or a binary vector. The intermediate vectors may be integrated into the Ti or Ri plasmid of the agrobacteria by homologous recombination due to sequences, which are homologous to sequences in the T-DNA. This also contains the vir-region, which is required for T-DNA transfer. Intermediate vectors cannot replicate in agrobacteria. The intermediate vector can be transferred to *Agrobacterium tumefaciens* by means of a helper plasmid (conjugation). Binary vectors are able to replicate in *E. coli* as well as in agrobacteria. They contain a selection marker gene and a linker or polylinker framed by the right and left T-DNA border region. They can be transformed directly into agrobacteria. The agrobacterium acting as host cell should contain a plasmid carrying a vir-region. The vir-region is required for the transfer of the T-DNA into the plant cell. Additional T-DNA may be present. Such a transformed agrobacterium is used for the transformation of plant cells. The use of T-DNA for the transformation of plant cells has been intensively studied and has been adequately described in standard review articles and manuals on plant transformation. Plant explants cultivated for this purpose with *Agrobacterium tumefaciens* or *Agrobacterium rhizogenes* can be used for the transfer of DNA into the plant cell. From the infected plant material (e.g. leaf pieces; stem segments, roots, but also protoplasts or suspension-cultivated plant cells) whole plants may be again regenerated in a suitable medium that may contain antibiotics or biocides to select the transformed cells.

Once the introduced DNA has been integrated into the plant cell genome, it is usually stable there and is maintained in the progeny of the originally transformed cell. It normally contains a selection marker, which imparts the transformed plant cells resistance to a biocide or an antibiotic such as kanamycin, G 418, bleomycin, hygromycin, methotrexate, glyphosate, streptomycin, sulfonylurea, gentamycin or phosphinotricin, etc. The individually selected marker should therefore allow the selection of transformed cells from cells lacking the introduced DNA. Alternative markers are also suitable for this purpose, such as nutritive markers, screening markers (such as GFP, green fluorescent protein). Naturally, it could also be done without any selection marker, although this would involve a fairly high screening expenditure. If marker-free transgenic plants are desired, there are also strategies available to the person skilled in the art, which allow subsequent removal of the marker gene, such as co-transformation and sequence-specific recombinases.

Transgenic plants are regenerated from transgenic plant cells by standard regeneration methods using known culture media. Using normal methods, including molecular biology methods, such as PCR and blot analyses, the plants thus obtained may then be analysed for the presence of introduced nucleic acid which codes for a protein having the enzymatic activity of an SGT.

The transgenic plants or transgenic plant cells can be any monocotyledonous or dicotyledonous plant or plant cell having an undesirably high content of sinapine. Preferably these are useful plants or cells of useful plants. Especially preferred are oil plants, which more preferably are rape, turnips, cereals, sugar beet, maize, sunflowers and flax. In principle, every useful plant, which is suitable for nutritional purposes, can be used to realize the invention.

The invention also relates to propagation material and agricultural products of the plants according to the invention, for example fruits, seeds, tubers, rhizomes (rootstocks), seedlings, cuttings and the like.

The specific expression of the SGT in the seeds of the plants or plant cells according to the invention can be detected and tracked using conventional molecular biological and biochemical techniques. The person skilled in the art is familiar with these techniques and he can easily select a suitable detection method, such as Northern blot analysis to detect SGT-specific RNA or to detect the accumulated level of SGT-specific RNA, respectively, or Southern blot analysis for the identification of the DNA sequences coding for SGT.

The invention furthermore relates to a method for producing plant protein having a reduced sinapine content compared to wild-type plant protein, comprising the following steps:

a) Transfer of a recombinant nucleic acid molecule or vector, which contains a DNA sequence encoding a protein having the enzymatic activity of an SGT to plant cells;

b) Regeneration of plants from the transformed plant cells;

c) Processing of the seeds of said plants from b) for the production of plant protein having a reduced sinapine content.

The present invention is explained in the following examples, which are intended to serve as illustrative of the invention and are by no means to be understood as restrictive.

EXAMPLES

A cDNA was isolated from rape (*Brassica napus*) which codes for the enzyme UDP-glucose: sinapate glucosyltransferase (SGT). As already mentioned above, the SGT catalyses the conversion of UDP-glucose and sinapic acid to 1O-sinapoylglucose (SinGlc), which in turn functions as activated acyl donor for the biosynthesis of sinapine.

a) Selection Method cDNA libraries were made from immature seeds and cotyledons from seedlings of *Brassica napus* var. Express. The modified λ-phage Uni-ZAP XR (Stratagene, La Jolla, Calif., USA) was used as vector. Glucosyltransferase-specific sequences were PCR-amplified using these cDNA libraries as template. Oligonucleotides derived from sequences of a highly conserved region in gluco syltransferases of the secondary metabolism in plants, namely the PSPG box (PSPG="plant secondary product glucosyl-transferase", protein sequence motif of the PSPG-Box: THCGWN; Hughes J. and Hughes M. A. (1994) *DNA Sequence* 5:41-49) were employed as PCR primers in the "forward" orientation. The following oligonucleotide was used among others as forward primer:

5'-ACNCAYTGYGGNTGGAAC-3'. The T7 primer was used as "reverse primer". The PCR reaction was carried out according to the following protocol (Eppendorf Mastercycler):

| "hot start": | 94° C. 4 min |
|---|---|
| 30 cycles: | 94° C. 1 min (denaturation) |
| | 56° C. 1 min (annealing) |
| | 72° C. 2 min (synthesis) |

The reaction mixture included:

| dATP, dGTP, dCTP, dTTP: | each 200 µM |
|---|---|
| primer (forward PSPG.T7): | each 100 pMol |
| rape cDNA banks from immature seeds or cotyledons | each 3 × 10$^6$ pfu* |
| Taq DNA polymerase (Appligene): | 1 unit |
| buffer for Taq polymerase | |
| water | |

(*pfu = plaques forming units)

The fragments amplified with PCR were labelled with α-[$^{32}$P]dATP and used as probes for hybridisation with Brassica napus-cDNA banks from seeds and cotyledons. Positive clones were isolated and the recombinant pBluescript-phagemides were excised using the in vivo "excision" technique (Stratagene) and transformed in E. coli (XL1-Blue MRF'; Stratagene).

The DNA sequence of all cDNA fragments isolated from Brassica napus in this way was determined from its 5' end. One of the cDNA sequences could be isolated both from the seeds ("SP15") and from the cotyledons ("CP5"), but was present at higher levels in the seeds. This sequence exhibited the highest identity to a "probable indole-3-acetate β-glucosyltransferase" (E71419) from Arabidopsis thaliana. Its reading frame encodes a protein with 497 amino acids (see SEQ ID No. 3). This protein exhibited high SGT activity. The coding sequence is deposited in the gene bank under accession number AF287143, and the protein sequence under accession number AAF98390; see also Milkowski et al. (2000) Planta 211:883-886.

b) Functional Test

As the cDNAs were inserted "downstream" from the E. coli lac promoter in the recombinant pBluescript phagemides, cloned genes were expressed in the E. coli host. E. coli cells of strain XL1-Blue MRF bearing phagemides with the inserts "CP5" and "SP15" were incubated with UDP-glucose and sinapic acid (60 min at 32° C.) to test for SGT activity. The cells were then lysed, the extracts precipitated with trifluoroacetic acid and the supernatants analysed with HPLC. In both cases, the elution profile resulted in the expected reaction product, which could be identified as sinapoylglucose by mass spectroscopy (LC-MS).

It was thus unambiguously demonstrated that the SGT-cDNA from Brassica napus had been cloned.

c) Tagging and Isolation of the SGT

The total cDNA sequence of the SGT of B. napus was amplified by PCR (without stop codon), and restriction sites for NcoI (at the 5'-end) and for BamHI (at the 3'-end) were introduced. The pBluescript vector containing the total SGT-cDNA from B. napus served as a template. The resulting PCR fragment was cloned into the vector pQE60 (Qiagen, Hilden) wherein the latter was cleaved with NcoI and BamHI. The constructs were transformed into the E. coli strain M15/pREP4 (Qiagen, Hilden).

The NcoI forward primer is given below; the same applies to the BamHI reverse primer.

d) Cultivation of E. coli Cultures and Induction of SGT Expression

The cells were cultivated at 37° C. in LB medium containing ampicillin (100 µg/ml) and kanamycin (25 µg/ml) as shaking culture (batch culture; 400 ml). In the early logarithmic growth phase (OD600=0.3), isopropyl-β-D-thiogalactoside (IPTG) was added (23.8 mg/ml) to induce expression of recombinant SGT, and the cells were then further cultivated overnight at 30° C. The cells were harvested by centrifugation (4000 rpm, 10 min, 4° C.) and frozen immediately at −80° C.

e) Protein Extraction and Purification

E. coli cells from a 12 liter culture (about 10 g dry weight) were suspended in 50 mM phosphate buffer (pH 8) additionally including 300 mM NaCl and 10 mM imidazole (cracking buffer/cell lysis buffer), and lysed via sonication. The specific SGT activity of the crude extract was 1.2 ncat/mg protein. The extract was loaded onto a cobalt agarose column (5 cm×2.6 cm inner diameter, flow rate 3 ml/min). After rinsing the column with cracking buffer non-specifically bound protein was further eluted with three column volumes of washing buffer (the same as the cracking buffer, but with 20 mM imidazole). The bound protein was eluted in a phosphate buffer containing 0.25 M imidazole. Active fractions were pooled and precipitated with 80% $(NH_4)_2SO_4$ (yield 3.7 mg). Further purification of the SGT was performed by gel filtration (Superdex 200, 26/60). Active fractions were pooled again and concentrated on Centricon filter units (yield 1.2 mg protein). A final purification step was carried out by hydrophobic interaction using phenylsuperose HR 5/5. The protein yield after this purification step was 570 µg and the specific activity was 400 ncat/mg protein. This corresponded to a 400-fold enrichment.

The molecular weight was determined by SDS gel electrophoresis and gel filtration on a superose 12 column. Gel electrophoresis gave a molecular weight of 62 kDa for the recombinant SGT; with gel filtration the result was 60 kDa.

f) Enzyme Assay

The eluate from the cobalt agarose column was precipitated with ammonium sulfate, desalted and then used for kinetic studies. 1 mg/ml bovine serum albumin was used for stabilisation.

The enzyme assay contained 20 mM UDP-glucose, 900 ng enzyme and various concentrations of sinapic acid (0.05; 0.1; 0.2; 0.4; 0.6; 1; 2; 4 mM). The buffer was 0.1 M MES (pH 6.0) and the incubation times were 2.5, 5 and 10 minutes. The Km for sinapic acid was calculated to be 0.13 mM.

g) Production of Transgenic Plants

Figure 1:
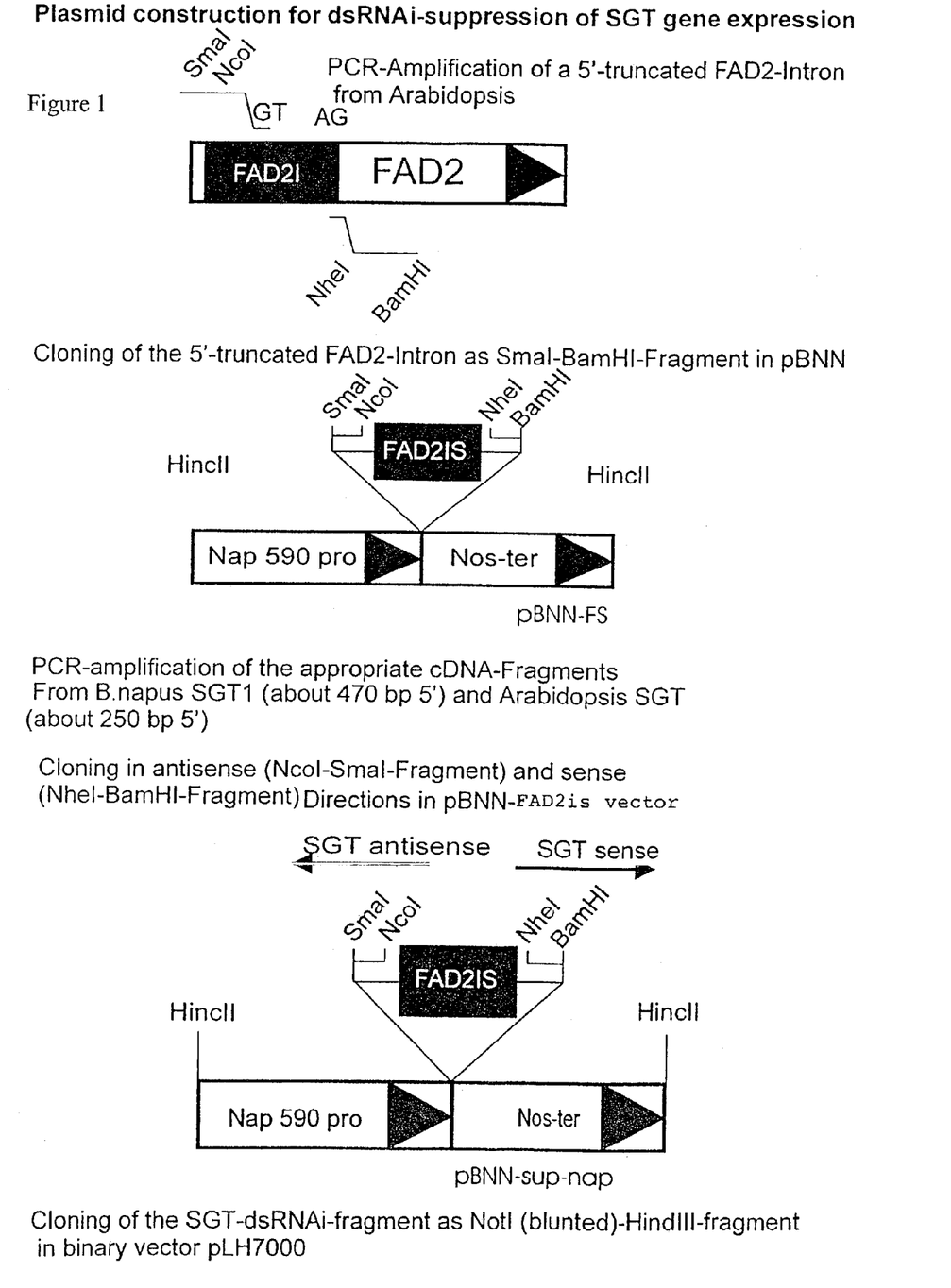
FIG. 1 shows an illustration of the preparation of the dsRNAI-suppression constructs.

The DNA sequence encoding the SGT protein was fused in anti-sense orientation with a seed-specific promoter, preferably the USP, LeB4 or napin promoter. The suppression assay of the double strand RNA interference (dsRNAI suppression) is also preferred; this assay is illustrated in FIG. 1.

The promoter-SGT anti-sense fusion or the dsRNAI suppression construct is transferred to a vector suitable for the transformation of rape, and the resulting construct is transferred to rape. Immature seeds are harvested from the transgenic rape plants. The content of 1-O-sinapoylglucose and of 1-O-sinapoylcholine (sinapine) in the crude extract is determined by HPLC analysis. The SGT activity is also measured.

Construction of Plasmids for the Suppression of SGT Expression in Transgenic Plants, Particularly in *Brassica Napus* and Arabidopsis.

Construction of a suppression vector for *Brassica napus*

Cloning of a shortened intron from *Arabidopsis*

First, a sequence from intron 1 of the FAD2 gene from the genomic DNA of *Arabidopsis thaliana* was amplified by PCR (Okuley et al. (1994) *Plant Cell* 6:147-158). The following primers were used for this purpose:

```
FADI-fw (forward):
ACCCGGGACTCCATGGTAAGTCGTATTCTCTCAACGCAATCG

FADI-NB (reverse):
TGGATCCAGTGCTAGCTGCAGAAAACCAAAAGC
```

The amplified fragment contains the 3'-region of the FAD2 intron (264 nucleotides) and is flanked by the restriction sites for SmaI and NcoI (at the 5'-end) and NheI and BamHI (at the 3'-end).

The amplified sequence is as follows:

5'-ACCCGGGACTCCATGGTAagtcgtat-tctcaacgcaatcgtttttatttctcacattatgccgcttctctactcttt attccttggtc-cacgcattttctatttgtggcaatc-cctttcacaactgatcceactttggateatgtctgaagactctcttgaa tcgttaccacttgtttcttgtgoat-gctctgttttttagaattaat-gataaaactattecatagtcttgagttttcagcttgttgattcttg cttttggttttctg-cagCTAGCACTGGATCCA-3'

(The sequence in lower case is the intron sequence; nucleotides written in capitals come from the added primer sequences)

This fragment was cloned as the SmaI-BamHI fragment into the vector pBNN, which was also digested with SmaI and BamHI. The vector pBNN is a derivative of pBIIKS, which contains the napin promoter 590 and the nos terminator. There are unique restriction sites for cloning between promoter and terminator. The resulting construct pBNN-FS carries the shortened FAD2 intron between the nap promoter and the nos terminator.

Cloning of an SGT fragment into pBNN-FS in anti-sense orientation

The plasmid pB-SGT1, pBluescript SK with the entire cDNA of *Brassica napus* SGT1 as EcoRI-XhoI fragment, was used as template, in order to amplify a specific fragment of the SGT1 sequence by PCR. The following primers were used:

```
Nco-SGT (forward):
GCTCGGTACCCCATGGAACTATCATCTTCTCC

Sma-SGT (reverse):
GTACCCGGGGAAGCTAGGCAAGCACAAGACTGG
```

The amplified fragment contains the 5'-region of the coding sequence of the SGT1-cDNA (470 nucleotides, starting with the A of the start codon) and is flanked by the restriction sites for NcoI (5') and SmaI (3').

```
GctcggtaccccATGGAACTATCATCTTCTCCTTTACCTCCTCATGTTAT

GCTTGTATCCTTCCCAGGACAAGGCCACGTTAATCCACTTCTTCGTCTCG

GCAAGCTCTTAGCTTCGAAGGGTTTACTCGTCACTTTTGTCACCACAGAA

TCATGGGGCAAAAAGATGCGAACCGCCAACAAGATTCAAGACCGAGCCCT

CAAACCTATCGGTAAAGGTTATCTCCGGTTCGATTTCTTCAACGATGGGC

TCCCTGAAGACGACGATGCAAGCAGAACCAACTTAACCATCCTCCGACCA

CAACTCGAGCTGGTCGGACAACAAGAGATCAAAAACCTCGTGAAACGTTA

CAAGGAAGTGATGAAACAGCCCGTGACGTGTCTCATCAACAACCCTTTCG

TCTCTTGGGTCTGTGACGTAGCCGAAGATCTTCAAATCCCCTGTGCTGTT

CTCTGGGTCCAGTCTTGTGCTTGCCTAGCTTCcccgggtac
```

(The sequence shown in capitals is the SGT1 sequence; nucleotides in lower case come from the added primer sequences)

This fragment was cloned as the NcoI-SmaI fragment into the pBNN-FS vector, which had been cleaved with NcoI and SmaI. The resulting construct pBNN-SGT-FS contains the SGT sequence in the anti-sense orientation between the nap promoter (nap=napin) and the shortened FAD2 intron.

Cloning of the SGT fragment in the sense orientation into pBNN-SGT-FS

The same SGT1 sequence as that used above for cloning in anti-sense orientation into the pBNN-FS was PCR-amplified using the following primers:

```
NheI-SGT (forward):
GTAGCTAGCATGGAACTATCATCTTCTCC

BamHI-SGT (reverse):
GTAGGATCCGAAGCTAGGCAAGCACAAGACTGG
```

The fragment was cloned as the NheI-BamHI fragment into the vector pBNN-SGT-FS cleaved with NheI-BamHI.

The resulting construct pBNN-sup-nap contains the following cassette (suppression cassette): nap 590-promoter—SGT1 (470 bp anti-sense) shortened FAD2-intron—SGT1 (470 bp sense)—nos-terminator.

Cloning of the suppression cassette from pBNN-sup-nap into the binary vector pLH7000

The plasmid pBNN-sup-nap was linearised, with the restriction enzyme NotI. The overlapping ends were filled in with Klenow polymerase. Cleavage was then carried out with the restriction enzyme HindIII. The DNA fragment containing the suppression cassette was isolated and cloned into the binary vector pLH7000, which had been subjected to double digestion with SmaI and HindIII (Hausmann and Töpfer (1999) Entwicklung von Plasmid-Vektoren in: Vorträge für die Pflanzenzüchtung (Development of Plasmid Vectors in: Lectures on Plant Breeding) Volume 45, "BioEngineering für Rapssorten nach Maβ, -Ergebnisse eines BMBF-Forschungsverbunds (Bioengineering for Rape Varieties as Required: Results of a BMBF Research Union", Eds. D. Brauer, G. Röbbelen and R. Töpfer, pages 155-171).

The resulting plasmid pLH7000-sup-nap was used for the transformation of rape. Transgenic plants having a reduced sinapine content compared to wild-type plants could be selected and intact plants could be regenerated.

Suppression vectors for transfer to *A. thaliana* were also constructed in a similar manner to that described above especially for *B. napus*. The only difference was that instead of the SGT1 fragment a fragment of AtSGT1 was cloned in anti-sense and sense orientations. AtSGT1 is described in Milkowski et al. (2000) *FEBS Letters* 486:183-184; the sequence for the SGT gene from *A. thaliana* is deposited in the gene database under the accession no. BAB02351. The amplified fragment contains the 5'-region of the coding sequence of the AtSGT1-cDNA (259 nucleotides, starting with the A of the start codon).

```
atggagctagaatcttctcctcctctacctcctcatgtgatgctcgtatcttttccagggcaaggccacgttaatccact tcttcgtcttggtaagctcttagcttcaaagggtttgctcataaccttcgtcaccactgagtcatgggcaaaaagatgc gaatctccaacaaaatccaagaccgtgtcctcaaaccggttggtaaaggctatctccggtatgatttcttcgacgacggg cttcctgaagacgacgaag
```

(The depicted sequence only shows the cloned fragment of AtSGT1; the flanking primer sequences are not shown).

The cloning strategy is shown in FIG. 1. dsRNAI stands for double strand RNA interference, as explained above.

It is evident that besides the vectors pBNN and pLH7000 mentioned above any other vector, which is suitable for the preparation of the desired anti-sense, or dsRNAI constructs or for plant transformation, may be used. The person skilled in the art working in the area of plant biotechnology is perfectly familiar with such vectors.

The invention claimed is:

1. A recombinant nucleic acid molecule comprising:
   a) regulatory sequences of a promoter that is active in plant cells; and
   b) operatively linked thereto a nucleic acid sequence encoding a protein having the enzymatic activity of a sinapate glucosyltransferase (SGT), or a fragment thereof, sufficient to inhibit the endogenous expression of SGT, wherein the nucleic acid sequence is selected from the group consisting of:
   i) nucleic acid sequences comprising a nucleotide sequence encoding the amino acid sequence given in SEQ ID NO: 3 or fragments thereof,
   ii) nucleic acid sequences comprising the nucleotide sequence given in SEQ ID NO: 1 or parts thereof;
   iii) nucleic acid sequences comprising a nucleotide sequence hybridising under stringent conditions with a complementary strand of the nucleic acid sequence from i) or ii), or comprising parts of this nucleotide sequence, wherein the stringent conditions include a hybridization buffer solution comprising about 7% SDS, about 250 mM NaCl, about 250 mM K-phosphate buffer at pH 7.0, and 1 mM EDTA and a hybridization temperature of about 58-60° C.; and
   iv) nucleic acid sequences having at least 98% identity with a nucleotide sequence from i) or ii).

2. The recombinant nucleic acid molecule according to claim 1, additionally comprising operatively linked to the coding nucleic acid sequence regulatory sequences that serve as transcription, termination and/or polyadenylation signals in plant cells.

3. The recombinant nucleic acid molecule according to claim 1 or 2, wherein the nucleic acid sequence originates from *Brassica*.

4. The recombinant nucleic acid molecule according to claim 3, wherein the nucleic acid sequence originates from *Brassica napus*.

5. The recombinant nucleic acid molecule according to claim 1 or 2, wherein the nucleic acid sequence is present exclusively in the anti-sense orientation.

6. The recombinant nucleic acid molecule according to claim 1 or 2, wherein the nucleic acid sequence is present in the sense and anti-sense orientations.

7. The recombinant nucleic acid molecule according to claim 1 or 2, wherein the nucleic acid sequence is present as a co-suppression construct.

8. The recombinant nucleic acid molecule according to claim 1 or 2, wherein the nucleic acid sequence is present as a double strand RNA interference suppression construct.

9. The recombinant nucleic acid molecule according to claim 1 or 2, wherein the promoter is active in plant seeds.

10. The recombinant nucleic acid molecule according to claim 9, wherein the promoter is a USP promoter.

11. The recombinant nucleic acid molecule according to claim 9, wherein the promoter is an LeB4 promoter.

12. The recombinant nucleic acid molecule according to claim 9, wherein the promoter is a napin promoter.

13. A vector comprising a recombinant nucleic acid molecule according to claim 1 or 2.

14. A micro-organism comprising a recombinant nucleic acid molecule according to claim 1 or 2.

15. The recombinant nucleic acid molecule of claim 1, further comprising washing after hybridization for 2×30 min at 55° C. to 60° C. with washing buffer I containing 2×SSC and 0.1% SDS followed by 2×30 min at 55° C. to 60° C. with washing buffer II containing 0.2×SSC and 0.1% SDS.

16. A recombinant nucleic acid molecule comprising a nucleic acid sequence encoding a protein having SGT activity or sufficient to inhibit the endogenous expression of SGT wherein the nucleic acid is selected from the group consisting of:
   a) nucleic acid sequences comprising a nucleotide sequence encoding the amino acid sequence given in SEQ ID NO: 3 or fragments thereof;
   b) nucleic acid sequences comprising the nucleotide sequence given in SEQ ID NO: 1 or parts thereof;
   c) nucleic acid sequences comprising a nucleotide sequence hybridizing under stringent conditions with a complementary strand of the nucleotide sequence from a) or b), or comprising parts of this nucleotide sequence, wherein the stringent conditions include a hybridization buffer solution comprising about 7% SDS, about 250 mM NaCl, about 250 mM K-phosphate buffer at pH 7.0, and 1 mM EDTA and a hybridization temperature of about 58-60° C.; and d) nucleic acid sequences having at least 98% identity with a nucleotide sequence from a) or b).

17. The nucleic acid sequence of claim 16, further comprising washing after hybridization for 2×30 min at 55° C. to 60° C. with washing buffer I containing 2×SSC and 0.1% SDS followed by 2×30 min at 55° C. to 60° C. with washing buffer II containing 0.2×SSC and 0.1% SDS.

18. Transgenic plant cells comprising a recombinant nucleic acid molecule according to claim 1 or 2.

19. Transgenic plants comprising a plant cell according to claim 18 and parts of these plants, transgenic agricultural products and transgenic propagating material of these plants, and the transgenic progeny of these plants.

20. The parts of the transgenic plants according to claim 19 selected from the group consisting of protoplasts, plant cells, calli, seeds, tubers and cuttings.

21. The transgenic plants or parts thereof according to claim 19 or 20, wherein the transgenic plants are oilseed plants.

22. The transgenic plants according to claim 21, wherein the transgenic plants are rapeseed.

23. A method for generating plants or plant cells having a reduced content of sinapine in comparison with wild-type plants or plant cells comprising the following steps:
   a) producing a recombinant nucleic acid molecule comprising:
      i) regulatory sequences of a promoter that is active in plant cells; and
      ii) operatively linked thereto a nucleic acid sequence encoding a protein having the enzymatic activity of an SGT, or a fragment thereof, sufficient to inhibit the endogenous expression of SGT, wherein the nucleic acid sequence is selected from the group consisting of:
         1) nucleic acid sequences comprising a nucleotide sequence encoding the amino acid sequence given in SEQ ID NO: 3 or fragments thereof;
         2) nucleic acid sequences comprising the nucleotide sequence given in SEQ ID NO: 1 or parts thereof;
         3) nucleic acid sequences comprising a nucleotide sequence hybridising under stringent conditions with a complementary strand of the nucleic acid sequence from i) or ii), or comprising parts of this nucleotide sequence, wherein the stringent conditions include a hybridization buffer solution comprising about 7% SDS, about 250 mM NaCl, about 250 mM K-phosphate buffer at pH 7.0, and 1 mM EDTA and a hybridization temperature of about 58-60° C.; and
         4) nucleic acid sequences having at least 98% identity with a nucleotide sequence from 1) or 2);
   b) transferring the nucleic acid molecule from a) to plant cells; and
   c) in case of the generation of plants, regenerating plants from the transformed plant cells.

24. A method of using a nucleic acid sequence that codes for a protein having the enzymatic activity of an SGT in anti-sense orientation for the reduction of the sinapine content in plants, comprising the following steps:
   a) producing a recombinant nucleic acid molecule according to claim 1 or 2, wherein the nucleic acid sequence is present exclusively in the antisense orientation;
   b) transferring the nucleic acid molecule from a) to plant cells; and
   c) regenerating plants from the transformed plant cells.

25. A method of using a nucleic acid sequence that codes for a protein having the enzymatic activity of an SGT as a co-suppression construct for the reduction of the sinapine content in plants, comprising the following steps:
   a) producing a recombinant nucleic acid molecule according to claim 1 or 2, wherein the nucleic acid sequence is present as a co-suppression construct;
   b) transferring the nucleic acid molecule from a) to plant cells; and
   c) regenerating plants from the transformed plant cells.

26. A method of using a nucleic acid sequence encoding a protein having the enzymatic activity of an SGT as a double strand RNA interference suppression construct for the reduction of the sinapine content in plants, comprising the following steps:
   a) producing a recombinant nucleic acid molecule according to claim 1 or 2, wherein the nucleic acid sequence is present as a double strand RNA interference suppression construct;
   b) transferring the nucleic acid molecule from a) to plant cells; and
   c) regenerating plants from the transformed plant cells.

27. A method of using a nucleic acid sequence encoding a protein having the enzymatic activity of an SGT in anti-sense or sense orientation to increase the content of lecithin in plants, comprising the following steps:
   a) producing a recombinant nucleic acid molecule according to claim 1 or 2, wherein the nucleic acid sequence is present in anti-sense or sense orientation;
   b) transferring the nucleic acid molecule from a) to plant cells; and
   c) regenerating plants from the transformed plant cells.

28. A method of using a nucleic acid sequence encoding a protein having the enzymatic activity of an SGT in anti-sense or sense orientation to increase the content of resveratrol in plants, comprising the following steps:
   a) producing a recombinant nucleic acid molecule according to claim 1 or 2, wherein the nucleic acid sequence is present in anti-sense or sense orientation;
   b) transferring the nucleic acid molecule from a) to plant cells; and
   c) regenerating plants from the transformed plant cells.

29. The method according to claim 23, wherein the recombinant nucleic acid additionally comprises, operatively linked to the coding nucleic acid sequence, regulatory sequences that serve as transcription, termination and/or polyadenylation signals in plant cells.

30. The method according to claim 23 or 29, wherein plant protein having a reduced content of sinapine compared to wild-type plant protein is obtained from the generated plants.

31. A method for generating plants or plant cells having a reduced content of sinapine in comparison with wild-type plants or plant cells comprising the following steps:
   a) producing a recombinant nucleic acid molecule comprising a nucleic acid sequence sufficient to inhibit the endogenous expression of SGT wherein the nucleic acid sequence is selected from the group consisting of:
      i) nucleic acid sequences comprising a nucleotide sequence encoding the amino acid sequence given in SEQ ID NO: 3 or fragments thereof;
      ii) nucleic acid sequences comprising the nucleotide sequence given in SEQ ID NO: 1 or parts thereof;

iii) nucleic acid sequences comprising a nucleotide sequence hybridizing under stringent conditions with a complementary strand of the nucleotide sequence from i) or ii), or comprising parts of this nucleotide sequence, wherein the stringent conditions include a hybridization buffer solution comprising about 7% SDS, about 250 mM NaCl, about 250 mM K-phosphate buffer at pH 7.0, and 1 mM EDTA and a hybridization temperature of about 58-60° C.; and iv) nucleic acid sequences having at least 98% identity with a nucleotide sequence from i) or ii); and b) transferring the nucleic acid molecule from a) to plant cells; and c) in case of the generation of plants, regenerating plants from the transformed plant cells.

32. The nucleic acid sequence of claim 31, further comprising washing after hybridization for 2×30 min at 55° C. to 60° C. with washing buffer I containing 2×SSC and 0.1% SDS followed by 2×30 min at 55° C. to 60° C. with washing buffer II containing 0.2×SSC and 0.1% SDS.

* * * * *